(12) United States Patent
Kim et al.

(10) Patent No.: US 10,418,129 B2
(45) Date of Patent: Sep. 17, 2019

(54) METHOD AND SYSTEM FOR DRUG VIRTUAL SCREENING AND CONSTRUCTION OF FOCUSED SCREENING LIBRARY

(71) Applicant: EWHA UNIVERSITY—INDUSTRY COLLABORATION FOUNDATION, Seoul (KR)

(72) Inventors: Wan Kyu Kim, Seoul (KR); Yea Jee Kwon, Seoul (KR); Hae Seung Lee, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 86 days.

(21) Appl. No.: 15/531,213

(22) PCT Filed: Nov. 26, 2015

(86) PCT No.: PCT/KR2015/012753
§ 371 (c)(1),
(2) Date: Feb. 22, 2018

(87) PCT Pub. No.: WO2016/085262
PCT Pub. Date: Jun. 2, 2016

(65) Prior Publication Data
US 2018/0218129 A1    Aug. 2, 2018

(30) Foreign Application Priority Data
Nov. 27, 2014   (KR) .......................... 10-2014-0167253

(51) Int. Cl.
*G16C 20/50* (2019.01)
*G16B 35/00* (2019.01)
*G16C 20/60* (2019.01)
*G16C 20/70* (2019.01)

(52) U.S. Cl.
CPC .............. *G16C 20/50* (2019.02); *G16B 35/00* (2019.02); *G16C 20/60* (2019.02); *G16C 20/70* (2019.02)

(58) Field of Classification Search
CPC ....................................................... G16C 20/60
USPC ........................................................... 702/19
See application file for complete search history.

(56) References Cited

U.S. PATENT DOCUMENTS

| | | | |
|---|---|---|---|
| 6,421,612 | B1 | 7/2002 | Agrafiotis et al. |
| 6,994,473 | B2 | 2/2006 | Nishibata et al. |
| 7,416,524 | B1 | 8/2008 | Lobanov et al. |

FOREIGN PATENT DOCUMENTS

| | | |
|---|---|---|
| KR | 10-2010-0047677 A | 5/2010 |
| WO | 03/038672 A1 | 5/2003 |

OTHER PUBLICATIONS

Creative commons, Commons Deed, "Analyses of Compound Set Using Structural Scaffold and Target Information," collection@ewha, (with English translation) (83 pages) (2014).
Pu et al., "Analysis of high-throughput screening assays using cluster enrichment," *Statistics in Medicine* 31:4175-4189 (2012).

*Primary Examiner* — Jerry Lin
(74) *Attorney, Agent, or Firm* — Seed IP Law Group LLP

(57) ABSTRACT

The present invention relates to a virtual drug screening method with high prediction accuracy based on various biological activities extracted from multiple drug screening data, without using structures or structural attribute information of target proteins or compounds; an intensive screening library constructing method; and a system therefor.

8 Claims, 4 Drawing Sheets

METHOD AND SYSTEM FOR DRUG VIRTUAL SCREENING AND CONSTRUCTION OF FOCUSED SCREENING LIBRARY

TECHNICAL FIELD

The present invention relates to bioinformatics, and more specifically, to a system and method which can predict with high accuracy the compounds having desired biological activities within a large database with less time and effort, and additionally, to a system and method for constructing an intensive screening library for efficient development of new drugs during the above process.

BACKGROUND ART

With regard to recent processes of new drug development, a virtual screening technology using a computer is being established in the related fields as a means to reduce time and effort. The background circumstances may include a significant increase in the amount of information relating to structure-activity relationship being accumulated by high throughput screening or combinatorial synthesis in addition to the marked improvement of calculator functions, a considerable increase in the information on the structures of target proteins due to the advances in genome-associated studies, etc.

Examples of such virtual screening technologies may include a ligand-based virtual screening, which is based on structural similarities between compounds that are traditionally known to have an activity on target proteins, i.e., the already-known information relating to structure-activity relationship; and a structure-based virtual screening like a protein-ligand docking using the conformational structure of target proteins.

The structure-based screening method is based on the concept that, in a case where multiple drugs bind in the vicinity of the active site of a target protein, the change in the amount of free energy in each binding process exhibits the strength and weakness of pharmaceutical activities, while any of the drugs is simultaneously in complementary relation with the protein. The structure-based screening method has advantages in that it can estimate the binding state between a target protein and a ligand and a pharmacological activity value thereof by computer, and can also anticipate an activity value with high accuracy prediction while not necessitating the information on structure-activity relationship. Although the method can distinguish true ligands from non-ligands, it is almost impossible to rank the quantitative order, and most virtual screening/docking programs have a limitation in that the flexibility of proteins cannot be considered. Additionally, a receptor structure (binding model) is essential, and the accuracy of prediction depends on the accuracy of structure. Furthermore, these programs also have a limitation in that the accumulation of structure-activity relationship is not linked to the improvement of the accuracy of prediction.

Meanwhile, unlike the structure-based screening method, the ligand-based virtual screening method, whose concept is based on the finding that a homology can be observed between the physicochemical parameters of the drugs that bind to the common areas, has an advantage in that it does not require a receptor structure (binding model). However, the ligand-based virtual screening method also has limitations in that the prediction beyond the already-known information is impossible, or that the accuracy of activity value prediction is low because the method requires advance information on pharmacological activities and the prediction accuracy depends on the quality and amount of the advance information.

The present inventors have made many efforts to overcome the limitations of the existing virtual screening technology described above, and as a result, they have confirmed that a virtual screening method, which does not use the information on the structures of target proteins or compounds or structural attributes thereof, unlike the existing methods, but instead performs a virtual screening based on various biological activities extracted from multiple drug screening data, thereby not only being capable of providing high prediction accuracy but also screening those compounds which have backbones entirely different from those of the existing compounds with known activities, can be provided, thereby completing the present invention.

(Patent Document 1) U.S. Pat. No. 6,421,612
(Patent Document 2) U.S. Pat. No. 6,994,473
(Patent Document 3) U.S. Pat. No. 7,416,524

DISCLOSURE

Technical Problem

The present invention has been made in order to solve the above problems.

Specifically, the present invention is intended to provide a system and method which can solve the problems relating to time and effort required in a large-scale drug screening and simultaneously output the compounds having similar activities with high accuracy in virtual screening.

Technical Solution

To solve the above problems, an exemplary embodiment of the present invention provides a virtual drug screening method, including:

(a) identifying an identifier (ID) by extracting a part indicating a compound from a compound set which is inputted thereinto through an input module, in an identification module;

(b) extracting random bioassay data from a bioassay database, in a bioassay selection module;

(c) calculating the odds thereof by confirming the presence of an activity in each of multiple compound sets comprised in the extracted bioassay data based on the predetermined hit compound score, in the bioassay selection module;

(d) selecting the bioassay data as data of hit enrichment bioassay in the bioassay selection module, when the odds calculated in step (c) are higher than or equal to the predetermined reference value;

(e) selecting compound sets comprising the identifier from the multiple compound sets, which are included in the selected bioassay data, in an enrichment score (ES) calculation module;

(f) calculating enrichment score (ES) for each compound set using the compound sets selected from step (e) and the presence of an activity confirmed in step (c), in the enrichment score (ES) calculation module; and (g) outputting the bioassay data as data which includes virtual analogous compounds in an output module, when the sum of the enrichment scores (ES) calculated in step (f) is higher than or equal to the predetermined reference value.

Additionally, preferably, when the bioassay database includes an "n" number of bioassay data, the bioassay data extraction in step (b) is performed by a sampling without replacement method, and the steps of (b) to (d) are repeated a total of n times by returning to step (b) after step (d).

Additionally, preferably, step (g) is (g1) outputting the compounds, which are included in the compound sets confirmed to be active in step (c) from the compound sets included in the bioassay data, as virtual analogous compounds in the output module, when the enrichment score (ES) calculated in step (f) is higher than or equal to the predetermined reference value.

Additionally, preferably, step (f) includes calculating each enrichment score (ES) according to Equation 1 below using the compound sets selected from step (e) and the presence of an activity confirmed in step (c):

$$ES = \text{Log}_2 \frac{\frac{HI}{HE}}{\frac{AI}{AE}}. \quad (1)$$

Additionally, preferably, step (f) includes: (f1) selecting only the compound sets which are confirmed to be active in step (c) and grouping them to the extent of a predetermined number of groups using the hit compound score confirmed in step (c), in the enrichment score (ES) calculation module; and (f2) calculating the enrichment score (ES) of each group using the compound sets selected from step (e) and the presence of an activity confirmed in step (c), in the enrichment score (ES) calculation module.

Additionally, preferably, the virtual drug screening method includes, after step (f2), (f3) estimating a regression equation by a regression analysis of the enrichment scores (ES) calculated in step (f2) according to a predetermined method, in the enrichment score (ES) calculation module; and (f4) calculating enrichment scores (ES) by inputting the score corresponding to the identifier which is inputted in step (a), in the enrichment score (ES) calculation module.

Additionally, preferably, step (g) includes (g2) outputting the bioassay data as data comprising virtual analogous compounds according to the order of the largest sum of the enrichment scores (ES) in the output module, when the sum of the enrichment scores (ES) calculated in step (f) is higher than or equal to the predetermined reference value.

To achieve the above objects, another embodiment of the present invention provides an intense screening library constructing method, which further includes, after step (d): (h) constructing an additional database by extracting the data of hit enrichment bioassay selected after repeating the steps of (b) to (d) a total of n times, in an intensive screening library constructing module.

To achieve the above objects, another embodiment of the present invention provides an intense screening library constructing method, which further includes, after step (g): (i) constructing an additional database by extracting the bioassay data, which is the subject to be outputted in step (g), after repeating the steps of (b) to (d) a total of n times, in the intensive screening library constructing module.

To achieve the above objects, another embodiment of the present invention provides a system for drug virtual screening and intensive screening library construction, which includes: an input module, into which a compound set is inputted; an identification module, which identifies an identifier by extracting a part indicating a compound from a compound set which is inputted thereinto through an input module; a bioassay selection module, which extracts random bioassay data from a bioassay database, calculates the odds thereof by confirming the presence of an activity in each of multiple compound sets included in the extracted bioassay data based on the predetermined hit compound score, and selects the bioassay data as data of hit enrichment bioassay when the calculated odds are higher than or equal to the predetermined reference value; an enrichment score (ES) calculation module, which selects compound sets including an identifier comprised from the multiple compound sets, which are included in the selected bioassay data, and calculates the enrichment score (ES) using the selected compound sets and the presence of a confirmed activity; and an output module, which outputs the bioassay data as data including virtual analogous compounds when the sum of the calculated enrichment scores (ES) is higher than or equal to the predetermined reference value.

Advantageous Effects of the Invention

The present invention can increase the success rate of a biological bioassay even for a compound included in a compound set with a small number of compounds by predicting the compound, which is predicted to have similar physiological and chemical activities, with high accuracy and within a short time.

Additionally, the accuracy can be further improved when regression analysis is applied.

Additionally, the intense screening library being constructed in the present invention can have a higher degree of accuracy as the method of the present invention is continued further.

Additionally, by comparing the enrichment scores with respect to compound sets, which are known to act on multiple various target proteins, as an input compound set, the present invention can be applied to estimate a target for a particular compound whose target is not known.

Additionally, the present invention can be applied to cases where the number and kind of targets are not accurately known, as those compounds discovered via phenotypic drug screening, and can be applied to discover unknown targets relating to the corresponding phenotype through the method and details of hit enriched bioassays to the compound set.

MODES FOR CARRYING OUT THE INVENTION

1. Definition of Terms

Figure 1:
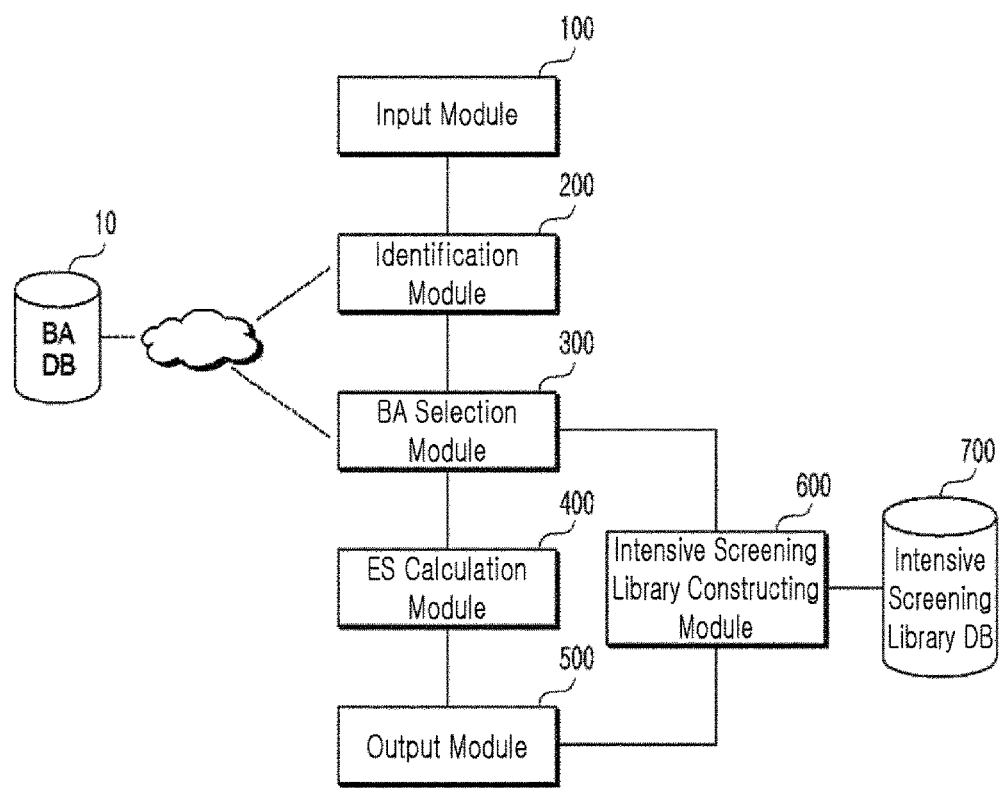
FIG. 1 shows a schematic chart illustrating the system according to the present invention.

As used herein, the term "compound set" refers to data which includes all of the information with regard to the structure, function, and backbone of a particular compound. For the purposes of identification, the identifier (ID) of the corresponding compound is included therein. The method for describing an identifier complies with the standard already known in the art.

As used herein, the term "bioassay data" refers to data with respect to the results of a bioassay which is already executed and known. Bioassay data includes multiple compound sets. For example, when the identifier of a particular compound is known, all of the bioassay data in which the particular compound is included can be extracted by inputting the corresponding identifier, and additionally, all of the compound sets in which the particular compound is included can be confirmed among many particular bioassay data.

As used herein, the term "hit compound" refers to a compound which shows a response to a condition (e.g., a target or particular protein) being inputted into a particular compound set. Hit compounds may be expressed by various indices, and in the present invention, they refer to the compounds which are inputted into a bioassay after quantification. Accordingly, the predetermination of hit compound scores as a reference enables the distinction between the presence and absence of an activity as a standard reference. The term "non-hit compound" is used as an opposite concept to the term "hit compound".

As used herein, the term "odds" refers to the ratio of hit compounds relative to non-hit compounds in the entirety of the data. For example, in a case where 1100 compound sets are included in a bioassay and the number of hit compounds is 100, the odds of hit compounds in the above bioassay are 0.1 (i.e., 100/1000).

As used herein, the term "enrichment" refers to a process in which unwanted data is filtered so as to secure desired data from multiple data. For example, in a case where the data in which data "A" is stored is to be confirmed, if 9,000 data are filtered, the remaining 1,000 data may be called "enriched data". Meanwhile, in the present invention, the degree of enrichment is called "enrichment score (ES)".

As used herein, the term "hit enriched bioassay" refers to a meaningful assay for confirming a virtual analogous compound of a compound desired by a user, i.e., a bioassay. While the predetermination of a reference value enables the distinction as a standard reference, the adjustment of the reference value by a user enables the control of the accuracy and amount.

As used herein, the term "receiver-operating characteristic (ROC) curve" refers to a curve in which hitting probability (i.e., sensitivity) is indicated on the Y axis and false alarm probability (i.e., 1-specificity) is indicated on the X axis for the purpose of confirming the efficiency of a particular prediction method, and in particular, the area under curve (AUC) refers to a value for the area under the curve.

As used herein, the term "system" must be understood as referring to an article which has a concept opposite to that of a method.

As used herein, the term "module" refers to a unit of a calculation means for the treatment of information, and it is not necessary that each module be physically separated. Each module may be established in only a single means or multiple modules may be established in a single means. For example, in a case where the system according to the present invention is established in an information processing terminal (i.e., a computer), the calculation activity of all of the modules may be performed in a single terminal or each module may individually perform the calculation activity in a separate terminal.

2. Explanation of System

Hereinafter, the system according to the present invention will be explained first referring to FIG. 1.

The system according to the present invention includes an input module 100, an identification module 200, a bioassay selection module 300, an enrichment score calculation module 400, an output module 500, an intense screening library constructing module 600, and an intense screening library database 700. Additionally, the system according to the present invention can upload or download information by being logged in to a bioassay database 10, which is additionally constructed by being connected through a web, etc.

The bioassay database 10 may be any database which includes bioassay data. However, the bioassay data must include multiple compound sets as described above, and it must be data stored in the format by which compounds can be automatically screened using an identifier identified in the identification module 200 to be described later.

An embodiment of the bioassay database 10 may be a bioassay database provided by the National Institutes of Health of the United States (https://pubchem.ncbi.nlm.nih.gov), but certainly the bioassay database is not limited thereto.

The input module 100 may be any means by which a user can input compound sets, for example, a keyboard, a mouse, a touch pad, etc.

The identification module 200 converts the compound set inputted by a user into a predetermined identifier. For this purpose, it is preferred that an identifier is stored by mapping per each compound in the bioassay database 10. In an embodiment described above, all of these identifiers are stored in the bioassay database provided by the NIH (USA). For example, in a case where the target protein is "ubiquitin carboxyl-terminal hydrolase 1", the identifier is stored as "O94782". The identification module 200 can automatically identify a compound-indicating part in a compound set, which is inputted through the input module 100, when connected to the bioassay database 10 through a web.

The bioassay selection module 300 performs the following functions.

First, the bioassay selection module 300 extracts random bioassay data from the bioassay database 10. As described above, a great deal of data is stored in the bioassay database 10, and the system according to the present invention confirms the data one by one, determining whether each data is the data of a hit enriched bioassay, to be described later, and to this end, the bioassay selection module 300 performs the function of selecting random bioassay data in a sampling without replacement method. That is, in a case where an n number of bioassay data is included in the bioassay database 10, random bioassay data will be extracted n times.

Second, the bioassay selection module 300 confirms the presence of an activity in each of the multiple compound sets which are included in the bioassay extracted based on the reference of the predetermined hit compound score and calculates the odds thereof.

Third, the bioassay selection module 300 selects the corresponding bioassay data as the data of a hit enriched bioassay when the calculated odds are higher than or equal to the predetermined reference.

The enrichment score calculation module 400 selects compound sets, in which the identifier of the compound to be confirmed being inputted by a user is included, from multiple compound sets included in the selected bioassay data and calculates the enrichment score (ES) using the selected compound sets and the confirmed presence of an activity. The specific method of calculation will be described in detail in "Explanation of Method" below.

The output module 500 outputs a virtual analogous compound, which is the final product, and the output module 500 may be any means, such as a monitor, a printer, etc., as long as it can output the result.

The intense screening library constructing module 600 performs the function of separately storing the bioassay data, which was confirmed as the data of hit enriched bioassays while performing the method according to the present invention, in the intense screening library database 700.

As described above, since the web-accessible general bioassay database 10 includes a great deal of data stored therein, it requires much time and effort to confirm the resulting product truly desired by the user, and the accuracy of the resulting product is also not very high. To overcome the above problem, multiple bioassay data are selected as the data of hit enriched bioassays as the method according to the present invention is performed, and by storing the same as an additional intense screening library database 700, time and effort can be significantly reduced while increasing the accuracy thereof when similar work is to be done in the future.

3. Explanation of Method

Figure 2:
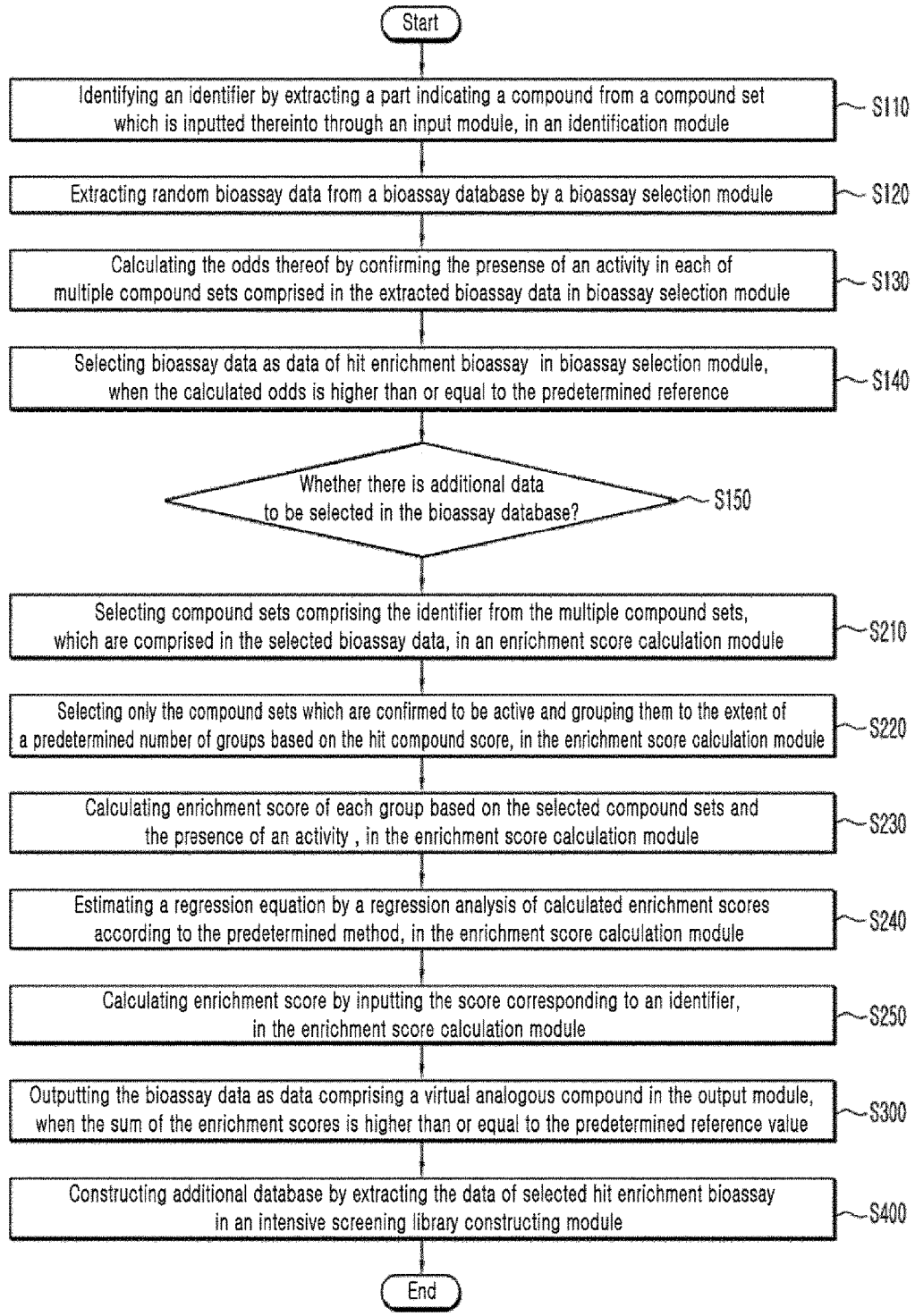
FIG. 2 shows a flow chart illustrating the method according to the present invention.

Referring to FIG. 2, the method according to the present invention is explained.

First, a virtual screening method is explained.

When a user inputs a compound whose analogous compounds are to be confirmed, through an input module 100, the input module 100 extracts the parts that indicate compounds from an inputted compound set and thereby identifies identifiers (S100). In particular, the data which is mapped in advance to the bioassay database 10 via a web, etc., and stored therein may be used.

Then, the bioassay selection module 300 extracts one random bioassay data by a sampling without replacement method (S120).

Then, the bioassay selection module 300 confirms the presence of an activity in each of multiple compound sets included in the extracted one bioassay data and calculates the odds thereof based on the hit compound score (S130). As described above, the hit compound score is a predetermined score and the method of calculating the odds is the same as explained above.

Then, the bioassay selection module 300 selects the bioassay data as data of the hit enrichment bioassay, when the calculated odds are higher than or equal to the predetermined reference value (S140). In particular, it is certainly possible to select whether a larger amount of data or more accurate data will be selected by variously controlling the reference.

Then, the bioassay selection module 300 confirms whether there is any unselected bioassay data, i.e., the presence of any bioassay data to be further selected. In a case when there is bioassay data to be further selected, the process returns to step S120 and is repeated.

In such a process, the steps of S120 to S140 are repeated to the extent of the number (n) of bioassay data stored in the bioassay database 10. As a result of such repetition, the data of hit enriched bioassays is selected from a large amount of data stored in the bioassay database 10. In the following process, the enriched scores will be calculated using only the data of the hit enriched bioassays.

Once the data of the hit enriched bioassays is selected, the enrichment score calculation module 400 confirms the compound sets, which include the identifiers, among the multiple compound sets included in the selected bioassay data (S210). Since multiple bioassay data are available and each bioassay data includes multiple compound sets, step S210 must be repeated several times.

Then, the enrichment score calculation module 400 calculates each enrichment score (ES) using the compound sets selected in step S210 and the presence of an activity confirmed first in step S130.

The process will be explained in more detail below.

First, the method for calculating enrichment score (ES) will be explained. Other methods for calculating enrichment score may be used, however, the present inventors have confirmed by many experiments that the method of expressing the enrichment score in a log scale shown in Equation 1 is most preferable. Since the Equation was confirmed to be preferable via the AUC values of ROC to be described later, the detail will be described later.

$$ES = \text{Log}_2 \frac{\frac{HI}{HE}}{\frac{AI}{AE}} \quad \text{[Equation 1]}$$

In the above equation,

HI, while including an identifier, represents the number of compound sets which are confirmed to be active;

HE, while not including an identifier, represents the number of compound sets which are confirmed to be inactive;

AI, being independent of the presence of an identifier, represents the number of total compound sets which are confirmed to be active; and AE, being independent of the presence of an identifier, represents the number of total compound sets which are confirmed to be inactive.

The presence of an identifier can be confirmed in step S210 and the presence of an activity is confirmed in step S130.

These may be represented in a table as shown below.

TABLE 1

|  | Including identifiers | Excluding identifiers |
| --- | --- | --- |
| Hit Compound Set (H) | HI | HE |
| Total Compound Set (A) | AI | AE |

For example, a case when the total number of compound sets is 20,400, the number of compound sets including identifiers identified through the identification module 200 is 200, and when the number of compound sets confirmed to be active among the total number of compound sets (20,400) is 300, the number of compound sets including identifiers identified through the identification module 200 is 100, may be expressed as shown in Table 2 below.

TABLE 2

|  | Including identifiers | Excluding identifiers |
| --- | --- | --- |
| Hit Compound Set (H) | 100 | 200 |
| Total Compound Set (A) | 400 | 20000 |

When the enrichment score (ES) of the bioassay data is calculated by the equation above in the enrichment score calculation module 400, it can be confirmed that ES=Log$_2$ 25.

The process will be explained in more detail below with regard to each step.

The enrichment score calculation module 400 first selects only the compound sets which are confirmed to be active and performs a grouping to the extent of a predetermined number of groups based on the hit compound score (S220). The enrichment score may be calculated without grouping, but the regression analysis through the grouping can further increase the accuracy (S220).

Then, the enrichment score calculation module 400 calculates the enrichment scores for each of the groups based on the compound sets selected in step S220 and the presence of an activity (S230).

Then, the enrichment score calculation module 400 estimates a regression equation by a regression analysis of calculated enrichment scores according to a predetermined method (S240). For example, the regression equation is estimated by extracting the scores corresponding to the compounds of multiple groups from the bioassay database 10 followed by determining the calculated enrichment scores as an observation value. Since the method for estimating the regression equation is a conventional technology widely known in the art, the detailed explanation thereof is omitted herein.

Then, the enrichment score calculation module 400 calculates an enrichment score by confirming the score corresponding to an identifier identified in the identification module 200 from the bioassay database 10, followed by inputting the score into the regression equation (S250). In particular, in a case when multiple enrichment scores calculated from the bioassay are given to a single identifier, the sum of the calculated enrichment scores will be the final enrichment score.

Through the above process, the enrichment scores were calculated for each bioassay data. As a result, as the bioassay data has higher enrichment scores, the data may be one which includes compounds that are similar to the compound inputted by the first user. Accordingly, when the sum of the calculated enrichment scores is higher than or equal to the predetermined reference value, the output module 500 estimates the enrichment scores as data with high similarity and thereby outputs the bioassay data as data including virtual analogous compounds.

In an alternative method, when the calculated enrichment score is higher than or equal to the predetermined reference value, the output module 500 may output only those compounds included in the compound sets confirmed to be active among the compound sets included in the bioassay data.

Then, an intensive screening library constructing method is explained.

There are two methods available.

One method is to construct an additional intensive screening library constructing module by extracting only the data of hit enrichment bioassay selected after repeating a total of n times, in the intensive screening library constructing module 600 (S400).

The other method is to construct as an additional database only the compound sets confirmed even among the data of hit enrichment bioassay selected after repeating a total of n times, in the intensive screening library constructing module 600.

4. Bioassay (1)

As the bioassay database 10, the above-described bioassay database (https://pubchem.ncbi.nlm.nih.gov) provided by the National Institutes of Health (NIH) of the United States was used. The compound to be confirmed was specified as "abhydrolase domain-containing protein 4 isoform 1 [*Mus musculus*]", inputted through the input module 100, and an identifier "ID: 720543" was identified by the identification module 200. The total number of the compound sets (AI+AE) was confirmed to be 369,939, and among them, the number of compound sets where the inputted identifiers (AI) were included was 995. The presence of an activity was classified by determining the hit compound score and the number of hit compound sets among the total compound sets was confirmed to be 2,005 (0.542%). Based on these results, the method according to the present invention was performed, and the results thereof were represented in graphs by ROC, and AUC values were calculated therefrom.

Figure 3:
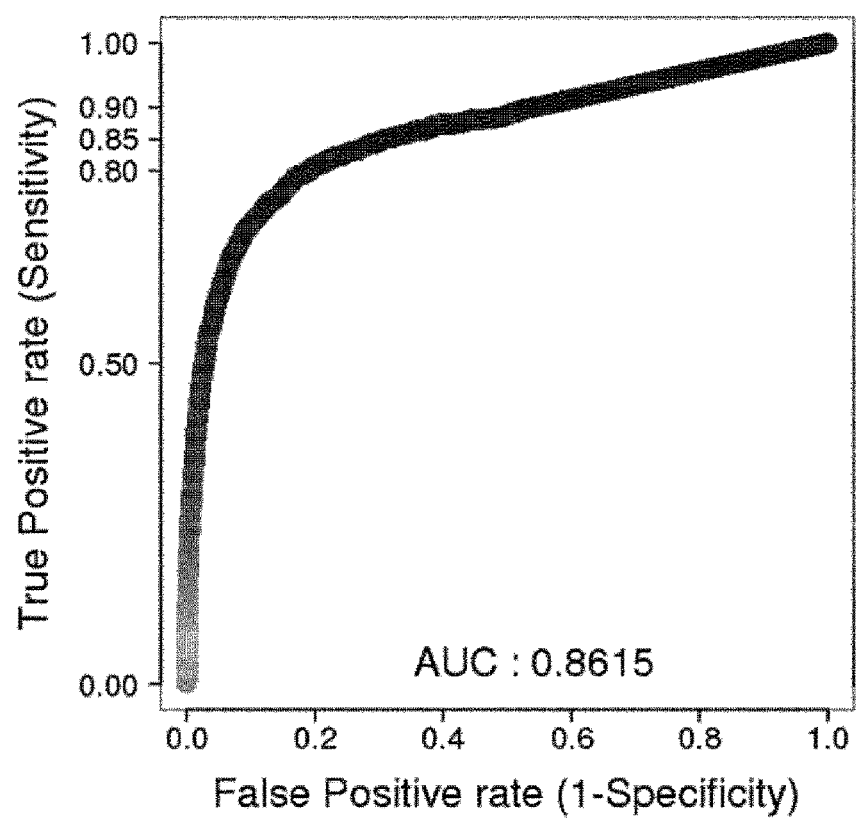
FIG. 3 shows ROC, which is the result of a bioassay (1) in which the method according to the present invention was applied.

The results of calculation were confirmed as shown in FIG. 3, and the AUC value was confirmed to be 0.8615. Generally, a prediction function is evaluated to be high when the AUC value exceeds 0.7, and it was thus verified that virtual analogous compounds can be confirmed by the method of the present invention with an excellent function of prediction.

5. Bioassay (2)

As the bioassay database 10, the above-described bioassay database (https://pubchem.ncbi.nlm.nih.gov) provided by the National Institutes of Health (NIH) of the United States was used. The compound to be confirmed was specified as "USP1 protein [*Homo sapiens*]", inputted through the input module 100, and an identifier "ID: 743255" was identified by the identification module 200. The total number of the compound sets (AI+AE) was confirmed to be 389, 560, and among them, the number of compound sets where the inputted identifiers (AI) were included was 339. The presence of an activity was classified by determining the hit compound score and the number of hit compound sets among the total compound sets was confirmed to be 904 (0.232%). Based on these results, the method according to the present invention was performed, and the results thereof were represented in graphs by ROC, and AUC values were calculated therefrom.

Figure 4:
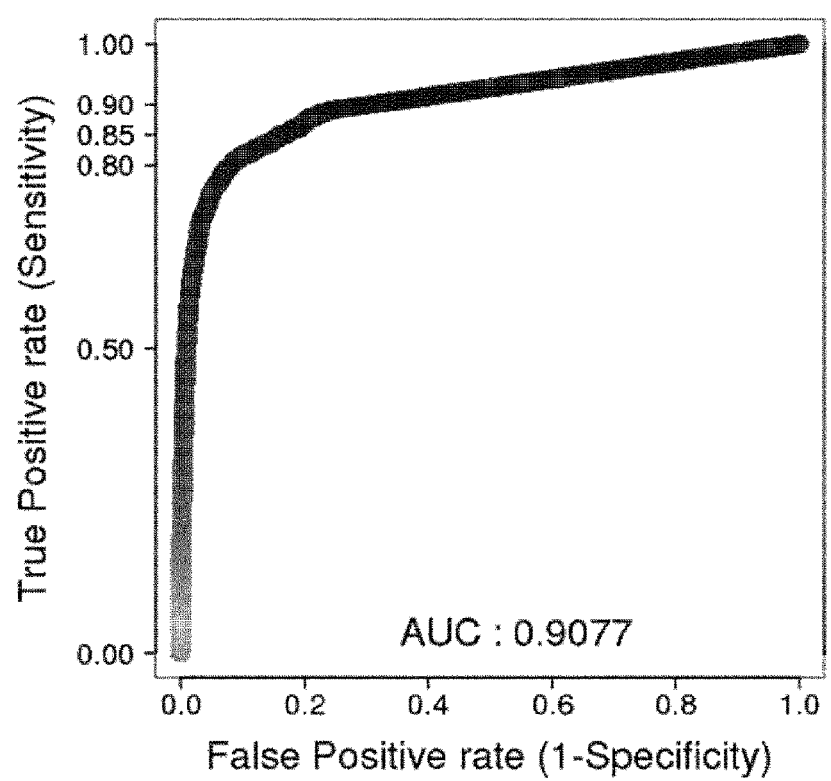
FIG. 4 shows ROC, which is the result of a bioassay (2) in which the method according to the present invention was applied.

The results of calculation were confirmed as shown in FIG. 4, and the AUC value was confirmed to be 0.9077. Accordingly, it was thus verified that virtual analogous compounds can be confirmed by the method of the present invention with an excellent function of prediction.

Although preferred embodiments of the present invention have been described in detail herein, it is to be understood that other modifications and variations may be effected by one of ordinary skill in the art without departing from the spirit and scope of the invention as defined by the appended claims.

REFERENCE NUMERALS

10: bioassay database
100: input module
200: identification module
300: bioassay selection module
400: enrichment score calculation module
500: output module
600: intensive screening library constructing module
700: intensive screening library database

The invention claimed is:

1. A method for performing a hit enriched bioassay, comprising:
    (a) identifying an identifier (ID) by extracting a part indicating a compound from a compound set which is inputted thereinto through an input module, in an identification module;
    (b) extracting random bioassay data from a bioassay database, in a bioassay selection module;

(c) confirming the presence of an activity in each of multiple compound sets comprised in the extracted bioassay data and calculating the odds thereof based on a predetermined hit compound score, in the bioassay selection module;

(d) selecting the bioassay data as data of a hit enrichment bioassay in the bioassay selection module, when the odds calculated in step (c) are higher than or equal to the predetermined reference value;

(e) selecting compound sets comprising the identifier from the multiple compound sets, which are comprised in the selected bioassay data, in an enrichment score (ES) calculation module;

(f) calculating an enrichment score (ES) for each compound set using the compound sets selected from step (e) and the presence of an activity confirmed in step (c), in the enrichment score (ES) calculation module, wherein the enrichment score (ES) is calculated according to the equation, $$ES = \text{Log}_2 \frac{\frac{HI}{HE}}{\frac{AI}{AE}}$$

wherein:
HI, while comprising an identifier, represents the number of compound sets which are confirmed to be active;
HE, while not comprising an identifier, represents the number of compound sets which are confirmed to be inactive;
AI, being independent of the presence of an identifier, represents the number of total compound sets which are confirmed to be active; and
AE, being independent of the presence of an identifier, represents the number of total compound sets which are confirmed to be inactive;

(g) outputting the bioassay data as data which comprises virtual analogous compounds in an output module, when the sum of the enrichment scores (ES) calculated in step (f) is higher than or equal to the predetermined reference value; and (h) performing a bioassay to confirm at least one virtual analogous compound of a compound.

2. The method for performing a hit enriched bioassay of claim 1, wherein when the bioassay database comprises an "n" number of bioassay data, the bioassay data extraction in step (b) is performed by a sampling without replacement method, and the steps of (b) to (d) are repeated a total of n times by returning to step (b) after step (d).

3. The method for performing a hit enriched bioassay of claim 1, wherein step (g) is:

(g1) outputting the compounds, which are comprised in the compound sets confirmed to be active in step (c) from the compound sets comprised in the bioassay data, as virtual analogous compounds in the output module, when the enrichment score (ES) calculated in step (f) is higher than or equal to the predetermined reference value.

4. The method for performing a hit enriched bioassay of claim 1, wherein step (f) comprises:

(f1) selecting only the compound sets which are confirmed to be active in step (c) and grouping them to the extent of a predetermined number of groups using the hit compound score confirmed in step (c), in the enrichment score (ES) calculation module; and (f2) calculating the enrichment score (ES) of each group using the compound sets selected from step (e) and the presence of an activity confirmed in step (c), in the enrichment score (ES) calculation module.

5. The method for performing a hit enriched bioassay of claim 4, further comprising after step (f2):

(f3) estimating a regression equation by a regression analysis of the enrichment scores (ES) calculated in step (f2) according to a predetermined method, in the enrichment score (ES) calculation module; and (f4) calculating enrichment scores (ES) by inputting the score corresponding to the identifier which is inputted in step (a), in the enrichment score (ES) calculation module.

6. The method for performing a hit enriched bioassay of claim 1, wherein step (g) comprises:

(g2) outputting the bioassay data as data comprising virtual analogous compounds according to the order of the largest sum of the enrichment scores (ES) in the output module, when the sum of the enrichment scores (ES) calculated in step (f) is higher than or equal to the predetermined reference value.

7. An intensive screening library constructing method using the method for performing a hit enriched bioassay of claim 2, further comprising, after step (d):

(i) constructing an additional database by extracting the data of hit enrichment bioassay selected after repeating the steps of (b) to (d) a total of n times, in an intensive screening library constructing module.

8. An intensive screening library constructing method using the method for performing a hit enriched bioassay of claim 2, further comprising after step (g):

(j) constructing an additional database by extracting the bioassay data, which is the subject to be outputted in step (g), after repeating the steps of (b) to (d) a total of n times, in the intensive screening library constructing module.

* * * * *